United States Patent

Wu et al.

[11] Patent Number: 5,474,964
[45] Date of Patent: Dec. 12, 1995

[54] HYDROCARBON ISOMERIZATION CATALYST AND USE THEREOF

[75] Inventors: An-Hsiang Wu; Marvin M. Johnson; Donald H. Kubicek; Fan-Nan Lin, all of Bartlesville, Okla.

[73] Assignee: Phillips Petroleum Company, Bartlesville, Okla.

[21] Appl. No.: 307,123

[22] Filed: Sep. 16, 1994

[51] Int. Cl.⁶ .............................. B01J 23/42; C07C 5/22
[52] U.S. Cl. .............................. 502/326; 585/748
[58] Field of Search .................... 585/748; 502/326

[56] References Cited

U.S. PATENT DOCUMENTS

| | | | |
|---|---|---|---|
| 2,824,114 | 2/1958 | Bostwick | 260/429.3 |
| 2,935,522 | 5/1960 | Samour | 260/429.3 |
| 2,950,174 | 8/1960 | Lagally | 23/202 |
| 3,028,297 | 4/1962 | Lagally | 162/181 |
| 3,694,475 | 9/1972 | Brook et al. | 260/429.5 |
| 3,892,791 | 6/1975 | Brook et al. | 260/429.5 |
| 4,119,675 | 10/1978 | Ryu | 260/672 T |
| 4,119,676 | 10/1978 | Ryu | 260/668 A |
| 4,149,993 | 4/1979 | Rao et al. | 252/442 |
| 4,201,696 | 5/1980 | Legendre et al. | 502/206 |
| 4,283,585 | 8/1981 | Legendre et al. | 585/482 |
| 4,312,785 | 1/1982 | Ryu | 252/429 R |
| 4,313,021 | 1/1982 | Ryu | 585/470 |
| 4,480,048 | 10/1984 | Bournonville et al. | 502/227 |
| 4,621,148 | 11/1986 | Barfurth et al. | 556/54 |
| 5,004,859 | 4/1991 | Schmidt et al. | 585/741 |
| 5,292,988 | 3/1994 | Wu | 585/747 |

OTHER PUBLICATIONS

DuPont Chemicals Material Safety Data Sheet 5886 PP, "Tyzor" Titanate, Sep. 17, 1993.

*Primary Examiner*—E. Rollins Cross
*Assistant Examiner*—Timothy H. Meeks
*Attorney, Agent, or Firm*—K. K. Brandes

[57] ABSTRACT

A catalyst composition is prepared by a method comprising impregnating alumina with at least one dissolved titanium compound (preferably a triethanolamine titanate) and at least one platinum compound, followed by treatment (at specific temperature conditions) with at least one organoaluminum chloride (preferably ethylaluminum dichloride), hydrogen chloride and at least one chloroalkane (preferably carbon tetrachloride). The thus-prepared catalyst composition is employed in the isomerization of saturated $C_4$–$C_8$ hydrocarbons (alkanes and/or cycloalkanes), preferably n-butane.

31 Claims, No Drawings

HYDROCARBON ISOMERIZATION CATALYST AND USE THEREOF

BACKGROUND OF THE INVENTION

In one aspect, this invention relates to the preparation of a platinum-containing catalyst composition. In another aspect, this invention relates to the use of this novel catalyst composition as a catalyst for isomerizing saturated $C_4$–$C_8$ hydrocarbons.

Supported platinum/chlorine-containing catalyst compositions and their use in alkane isomerization reactions are well known, and are described in the patent literature, e.g., in U.S. Pat. Nos. 5,004,859 and 4,149,993. However, there are ever present incentives for the development of new Pt/Cl-containing catalyst compositions and new methods for preparing them.

SUMMARY OF THE INVENTION

It is an object of this invention to provide a novel method for preparing a supported, Pt/Cl-containing catalyst composition. It is another object of this invention to provide a novel catalyst composition prepared by this preparation method. It is a further object of this invention to employ this novel catalyst composition in reactions for isomerizing saturated $C_4$–$C_8$ hydrocarbon. Other objects and advantages will become apparent from the detailed description and the appended claims.

In accordance with this invention, a method of preparing a solid platinum- and chlorine-containing composition comprises:

(a) impregnating alumina (in any order) with at least one dissolved titanium compound and at least one platinum compound, wherein about 0.4–0.6 weight-% Ti is incorporated into said alumina;

(b) heating the impregnated alumina obtained in step (a) at a temperature of about 300°–650° C. for a time period of at least about 10 minutes;

(c) contacting the calcined material obtained in step (b) with at least one organoaluminum chloride;

(d) calcining (heating) the material obtained in step (c) at a temperature of about 600°–700° C. for a time period of at least about 10 minutes; and (e) treating (in any order) the material obtained in step (d) with a HCl-containing gas at a temperature of about 450°–600° C. for a time period of at least about 10 minutes and with a gas containing at least one chloroalkane at a temperature of about 250°–350° C. for a time period of at least about 10 minutes.

In one preferred embodiment, the at least one titanium compound is at least one alkanolamine titanate, more preferably a triethanolamine titanate. In another preferred embodiment, the at least one organoaluminum chloride is ethylaluminum dichloride. In a further preferred embodiment, the chloroalkane is carbon tetrachloride.

In still another preferred embodiment, step (a) is carried out in three sub-steps: (a1) the alumina is first impregnated with at least one dissolved alkanolamine titanate, (a2) the titanate-impregnated alumina is calcined (heated) at a temperature of about 300°–600° C. for a time period of at least about 10 minutes, and (a3) the thus-obtained calcined material is impregnated with the at least one dissolved platinum compound.

In a still further preferred embodiment, step (e) is carried out in two sub-steps: (e1) first treating the material obtained in step (d) with an HCl-containing gas at a temperature of about 500°–600° C. for a time period of at least about 10 minutes, and (e2) thereafter treating the material obtained in step (e1) with a chloroalkane-containing gas at a temperature of about 250°–350° C. for a time period of at least about 10 minutes.

Also in accordance with this invention, a catalyst composition is provided which has been prepared by one of the preparation methods described above.

Further in accordance with this invention, at least one saturated feed hydrocarbon containing 4–8 carbon atoms per molecule selected from the group consisting of alkanes and cycloalkanes is isomerized to at least one corresponding saturated hydrocarbon isomer in the presence of hydrogen gas and a catalyst composition of this invention which has been prepared by one of the preparation methods described above.

DETAILED DESCRIPTION OF THE INVENTION

(A) Catalyst Preparation

Any suitable alumina material can be used in steps (a) of the preparation method of this invention. Suitable aluminas include (but are not limited to) hydrated aluminas (such as boehmite, pseudoboehmite, bayerite), alpha-alumina, beta-alumina, gamma-alumina, delta-alumina, eta-alumina and theta-alumina, preferably gamma-alumina. The alumina material generally has a surface area (determined by the BET method of Brunauer, Emmett and Teller employing $N_2$) of about 100–400 $m^2$/g, a pore volume (measured by nitrogen intrusion porosimetry) of about 0.2–1.0 $cm^3$/g, and a particle size of about 8–200 mesh. The alumina particles can be spherical, cylindrical, trilobal, or can have any other suitable shape. The presently preferred alumina particles are cylindrical extrudates.

Any soluble (preferably water-soluble) titanium compound can be used in step (a) of the preparation method of this invention. Preferred Ti compounds are water-soluble alkanolamine titanates. These compounds are well known and have been described in the patent literature, such as in U.S. Pat. Nos. 2,824,114, 2,935,522, 2,950,174, 3,028,297, 3,694,475, 3,892,791 and 4,621,148, the disclosures of which are incorporated herein by reference. They are generally prepared by reacting one mole of a tetralkyl orthotitanate (also referred to as tetralkyl titanate) with 1–4 (preferably 2) moles of an alkanolamine selected from the group consisting of ethanolamine, diethanolamine, triethanolamine (preferred), monoisopropylamine, diisopropylamine and triisopropylamine. Each of the alkyl (R) groups (which may be the same as or different from one another) of the tetralkyl titanate, $Ti(OR)_4$, contains 2–4 carbon atoms, and preferably is the isopropyl group. The more preferred alkanolamine titanate used in step (a) of the method of this invention has been prepared by the reaction of 1 mole of tetraisopropyl titanate, $Ti(OR)C_3H_5)_4$, with 2 moles of triethanolamine, also referred to as tri(2-hydroxyethyl)amine, thus forming primarily diisopropyl-bis(triethanolamine) titanate. Presently most preferred is a solution containing 80 weight-% of diisopropyl-bis(triethanolamine) orthotitanate and 20 weight-% of isopropanol. This solution is commercially available, e.g., from DuPont de Nemours and Co., Wilmington, Del., under the product designation of "TYZOR" (a registered trademark of DuPont) TE TITANATE.

Any suitable platinum compound which is water-soluble can be used in the preparation method of this invention. These compounds are well known and include (but are not limited to) platinum dichloride, platinum tetrachloride, hexachloroplatinic(IV) acid, ammonium hexachloroplatinate(IV), tetrammineplatinum(II) chloride, tetrammineplatinum(II) carbonate, tetrammineplatinum(II) hydroxide, dichlorodiammineplatinum(II), tetrachlordiammineplatinum(IV), platinum(II) nitrate, platinum(IV) nitrate, hexammineplatinum(II) nitrate, hexammineplatinum(IV) nitrate, diammineplatinum(IV) nitrite, diammineplatinum(II) oxalate, and many other complex or coordination compounds of divalent and tetravalent platinum. Presently preferred is hexachloroplatinic acid, $H_2PtCl_6$.

The alumina material can be impregnated with at least one dissolved Ti compound (preferably alkanolamine titanate) and at least one dissolved platinum compound substantially simultaneously, e.g., by dissolving the Ti and Pt compounds in water, and then contacting alumina with this solution. However, it is presently preferred to carry out the impregnation in separate steps: first impregnating alumina with an aqueous solution of an alkanolamine titanate, drying the thus-impregnated alumina and calcining it (generally in air) at about 300°–550° C. for about 0.5–20 hours, and then impregnating the calcined Ti-containing with an aqueous solution of a platinum compound. The concentration of the alkanolamine titanate in the first aqueous impregnating solution generally is about 3–15 mole/l, and the concentration of the platinum compound in the second aqueous impregnating solution is about 1–2 mole/l. The weight ratios of dissolved alkanolamine titanate and dissolved platinum compound is such as to incorporate about 0.4–0.6 weight-% Ti into and about 0.1–0.6 (preferably 0.2–0.4) weight-% Pt into the alumina material.

In step (b), the Ti/Pt-impregnated alumina material is dried (e.g., at about 80°–150° C.), and calcined at a temperature of about 300°–650° C. (preferably 450°–550° C.) for a time period of about 0.5–20 hours (preferably about 2–4 hours). This calcining step can be done in an inert atmosphere (i.e., $N_2$, He, Ar) or in an $O_2$-containing atmosphere (e.g., air).

In step (c) of the preparation method of this invention, the calcined Ti/Pt-containing alumina is contacted with at least one suitable organoaluminum chloride. Examples of such organoaluminum chlorides include (but are not limited to) methylaluminum dichloride, methylaluminum sesquichloride, dimethylaluminum chloride, ethylaluminum chloride, ethylaluminum sesquichloride, diethylaluminum chloride. Presently preferred is ethylaluminum dichloride. These organoaluminum compounds are easily hydrolyzed (by water) and thus should be handled and applied in a dry environment. Preferably they are dissolved in a dry organic hydrocarbon solvent, such as a $C_6$–$C_{10}$ cycloalkane, benzene, toluene, ethylbenzene, or a xylene. The presently preferred solvent is cyclohexane.

Generally, the weight ratio of the organoaluminum chloride to the Ti/Pt-impregnated alumina is in the range of about 0.05:1 to about 1:1, preferably about 0.1:1 to about 0.2:1. It is presently preferred to dissolve the organoaluminum chloride in an essentially water-free solvent and then contact the Ti/Pt-impregnated alumina with the solution (which generally contains about 5–50 weight-% of the organoaluminum chloride) at a temperature of about 10°–50° C. for a time period of about 0.5–5 hours (preferably about 1–2 hours). However, it is within the scope of this invention (yet less preferred) to vaporize the organoaluminum chloride and contact the thus-vaporized compound with the Ti/Pt-impregnated alumina at the above-recited weight ratio for about 0.5–2 hours at a temperature of about 500°–700° C.

In step (d), the organoaluminum chloride-treated material obtained in the previous step is calcined at a temperature of about 600°–700° C. (preferably about 625°–675° C.) for a period of time of about 0.5–20 hours (preferably about 0.5–2 hours). This calcining can be in an inert gas atmosphere (e.g., $N_2$, He, Ar) or in an $O_2$-containing atmosphere (e.g., air).

Chlorination step (e) is carried out by sequential heating with an HCl-containing gas and with a chloroalkane-containing gas, or vice versa. Preferably, the HCl treatment step is carried out first, at a temperature of about 500°–600° C. (more preferably about 525°–575° C.) for a period of time of about 0.2–20 hours (preferably about 0.5–2 hours), wherein HCl is generally diluted with an inert gas (e.g., $N_2$, He, Ar) such that the HCl-containing gas contains about 10–30 weight-% HCl. Then the treatment with the chloroalkane-containing gas is carried out at a temperature of about 250°–350° C. (preferably about 275°–325° C.) for a period of time of about 0.2–20 hours (preferably about 0.5–2 hours), wherein the vaporized chloroalkane is generally diluted with an inert gas (e.g., $N_2$, He, Ar). Generally, the chloroalkane-containing gas contains about 10–30 weight-% of the chloroalkane.

The chloroalkane employed in the chlorination step can be any suitable volatile chloroalkane. Generally, the chloroalkane contains 1–4 carbon atoms per molecule and 1–6 chlorine atoms per molecule. Examples of suitable chloroalkanes include (but are not limited to) chloromethane, dichloromethane, trichloromethane (chloroform), carbon tetrachloride, chloroethane, 1,1-dichloroethane, 1,2-dichloroethane, trichloroethanes, tetrachloroethanes, hexachloroethane, 1-chloropropane, 2-chloropropane, 1,2-dichloropropane, 1,3-dichloropropane, 2,2-dichloropropane, trichloropropanes, tetrachloropropanes, chlorobutanes, 1-chloro-2-methyl-propane, dichlorobutanes, trichlorobutanes, tetrachlorobutanes, and the like, and mixtures thereof. Carbon tetrachloride is presently preferred.

The finished catalyst composition generally contains about 0.4–0.6 weight-% Ti, about 0.1–1 (preferably about 0.2–0.4) weight % Pt and about 2–7 (preferably about 4–5) weight % Cl. The surface area, pore volume, shape and particle size of the finished catalyst composition are approximately the same as those of the alumina starting material (recited above).

(B) Alkane Isomerization

The catalyst of this invention is generally employed in the isomerization of saturated $C_4$–$C_8$ hydrocarbons (preferably normal alkanes). Examples of suitable feed hydrocarbons include (but are not limited to) normal butane, normal pentane, normal hexane, normal heptane, normal octane, cyclohexane, methylcyclopentane, cycloheptane and methylcycloheptane (more preferably n-butane), generally in the presence of hydrogen. These so-called hydroisomerization processes are well known and have been described in the patent literature (e.g., in U.S. Pat. Nos. 4,149,993 and 5,004,859). Generally, hydrogen is mixed with the saturated feed hydrocarbon to form a feed mixture which is contacted with the isomerization catalyst of this invention contained in an isomerization zone. The concentration of the hydrogen in the feed mixture during this contacting step shall be such as to provide a hydrogen:hydrocarbon molar ratio of at least about 0.01:1, generally about 0.01:1 to about 5:1, preferably about 0.02:1 to about 2:1. The basic isomerization reaction conditions are well known and can be varied to achieve the desired conversion of the feed hydrocarbon to the desired isomer in a manner known in the art. Also, the recovery of the product isomer from the reaction mixture can be carried out by any suitable separation technique, such as fractional distillation. Isomerization of normal butane (n-butane) to isobutane is the presently preferred reaction carried out with the catalyst composition of this invention.

Generally, the saturated feed hydrocarbon and $H_2$ are contacted with the catalyst (generally present in a fixed bed) at a reaction temperature of at least about 200° F., preferably at a temperature of about 200°–500° F. In the preferred case of n-butane isomerization, the temperature is generally about 250°–400° F. Generally, the liquid hourly space velocity of the saturated hydrocarbon feed stream, i.e., cc of liquid feed hydrocarbon per cc of catalyst per hour, is about 0.1 to about 15. Generally, the reaction pressure is within the range of 200 psig to about 1500 psig in the isomerization zone. The gas hourly space velocity of the hydrogen feed stream is generally about 10–2,000 (preferably about 50–950) cc $H_2$ per cc catalyst per hour (so as to give the above-recited $H_2$:hydrocarbon ratio). In order to activate the catalyst and to retard its deactivation during the isomerization reaction, about 0.001 to about 1 weight percent chloride is frequently added to the alkane feed, generally in the form of at least one chloroalkane (described above), preferably carbon tetrachloride, chloroform, ethyl chloride or isopropyl chloride.

When the catalyst employed in the hydroisomerization process has lost its activity to the extent that the desired alkane conversion can no longer be attained at the desired reaction temperature, the catalyst can be reactivated by turning off the flow of the saturated feed hydrocarbon while maintaining the flow of the $H_2$ stream through the isomerization catalyst, generally at about the same gas hourly space velocity of $H_2$ as in the isomerization reaction. The temperature in this reactivation step is generally about the same as in the isomerization reaction, but may be readjusted upward or downward to maximize the reactivation effect. In the preferred reactivation mode, a reducing gas stream consisting essentially of hydrogen is passed through the partially deactivated isomerization catalyst bed at a temperature of about 50°–400° F. (preferably about 250°–330° F.) and a GHSV (gas hourly space velocity) of about 10–2,000 cc $H_2$ per cc catalyst per hour (more preferably about 50–950 cc/cc/hour), for a time period of about 2 hours to about 10 days (more preferably about 5 hours to about 7 days). Thereafter, the reactivated catalyst is redeployed in the alkane hydroisomerization of saturated $C_{4-C8}$ hydrocarbons, as described above.

The following examples are presented to further illustrate the present invention and are not to be construed as unduly limiting the scope of this invention.

EXAMPLE I

This example illustrates the preparation of various alumina-supported platinum catalysts.

Catalyst A (Control) was prepared by impregnating 38.56 grams (40 cc) of a Pt/Al$_2$O$_3$ catalyst composition (containing about 0.3 weight-% Pt; surface area:215 m$^2$g; provided by UOP, Des Plaines, Ill.) with 18.88 grams of a 30 weight-% ethylaluminum dichloride (EADC) solution in cyclohexane for about 30 minutes under an argon gas atmosphere. The thus-treated material was dried in an argon gas stream at room temperature for about 20 hours, heated in a helium gas stream at 650° C. for about 1 hours, and allowed to cool to room temperature. The cooled material weighed 41.05 grams. It was divided into three portions, and each portion was heated as follows: first in a stream of pure helium gas at a temperature ranging from room temperature to 200° C., then in a gas stream containing 80 volume-% helium (He) and 20 volume-% hydrogen chloride (HCl) while the temperature was raised from 200° C. to 550° C. within a time period of 35 minutes, and thereafter in the 80/20 He/HCl gas stream at 550° C. for 1 hours, followed by cooling the material in the 80/20 He/HCl gas stream from 550° C. to 200° C. within a time period of 35 minutes, and then cooling the HCl-treated material in a pure helium stream to room temperature. 15.40 grams (20 cc) of the HCl-treated material was heated as follows: first in a stream of pure He gas at a temperature ranging from room temperature to 200° C., then in a gas stream containing 80 volume-% helium and 20 volume-% carbon tetrachloride (CCl$_4$) while temperature was raised from 200° C. to 300° C. within a period of 20 minutes, and thereafter in the 80/20 He/CCl$_4$ gas stream at 300° C. for 1 hour, followed by cooling the material in the He/CCl$_4$ gas stream from 300° C. to 200° C. within a time period of 10 minutes, and then cooling the CCl$_4$-treated material in a pure helium stream to 180° C.

Catalyst B (Control) was prepared in the same manner as Catalyst A, with the following exceptions: the Pt/Al$_2$O$_3$ staring material was a reforming catalyst provided by Criterion Catalyst Company, Houston, Tex. (containing about 0.3 weight-% Pt, surface area: 207 m$^2$/g), a sample of 29.00 grams (40 cc) of the starting material was employed, 14.0 grams of the 30 weight-% ethylaluminum dichloride (EADC) solution in cyclohexane was employed, the calcined EADC-treated material weighed 30.80 grams, this amount was divided into two portions, and each portion was heated in He in 80/20 He/HCl (as described for Catalyst A) and in 80/20 He/CCl$_4$ (as described for Catalyst A), and thereafter cooled in He/CCl$_4$ and He (as described for Catalyst A).

Catalyst C (Control) was prepared by mixing 120.0 grams of alumina (provided by Criterion Catalyst Company) and a solution of 6.12 grams of "TYZOR" (a registered trademark of DuPont) TE TITANATE (provided by DuPont Chemicals, Wilmington, Del.; containing 80 weight-% diisopropyl-bis(triethanolamine) orthotitanate, also referred to as isopropoxy(triethanolaminato)titanium, and 20 weight-% isopropanol) in 61.88 grams of water. The flask containing the formed mixture of alumina, " TYZOR" (a registered trademark of DuPont) TE TITANATE and water was then attached to an aspirator pump for 5 hours. The substantially dried material (weighing 130.58 grams) was heated in helium at 400° C. for 16 hours, then heated in oxygen gas at 500° C. for 16 hours, and cooled from 500° C. to 160° C. in oxygen gas within a period of 1 hour. The obtained calcined material, which weighed 117.6 grams, was impregnated (by incipient wetness) with a solution containing 1.02 grams of hexachloroplatinic acid, 65.62 grams of water and 1.36 grams of HCl. The impregnated material was substantially dried by means of an aspirator pump for 2.5 hours, calcined in a stream of oxygen gas at 500° C. for 16 hours, treated with flowing hydrogen gas at 400° C. for 4 hours, and allowed to cool in a stream of hydrogen gas to 150° C. within a time period of 1 hours. Catalyst C contained 0.42 weight-% Ti and 0.33 weight-% Pt.

Catalyst D (Control) was prepared by mixing 14.7 grams of Criterion alumina with an aqueous Tyzor® TE solution (both described in the preparation of Catalyst C). The obtained mixture was dried/calcined, impregnated with an aqueous $H_2PtCl_6$ solution, dried and calcined (as described for Catalyst C). The Pt-impregnated material was then treated with 7.00 grams of a 30 weight-% solution of ethylaluminum dichloride (EADC) in cyclohexane for about 30 minutes under an argon atmosphere, followed by drying the EADC-treated material at room temperature in an argon gas stream, heating it in a helium gas stream at 650° C. for 1 hour, and cooling it to about 150° C. Catalyst D contained 0.42 weight-% Ti and 0.33 weight-% Pt.

Catalyst E (Control) Catalyst E was prepared substantially in accordance with the procedure for Catalyst D, except that the material which had been treated with EADC and heated at 650° C. in He was subsequently treated as follows: heated in He (to 200° C.), heated in 80/20 He/$CCl_4$ so as to raise the temperature from 200° C. to 300° C. within 20 minutes, and then heated in 80/20 He/$CCl_4$ at 300° C. for 1 hour, followed by cooling in 80/20 He/$CCl_4$ from 300° C. to 200° C. within 20 minutes, and cooling in He from 200° C. to 180° C., i.e., essentially in accordance with the $CCl_4$ treatment procedure described for Catalyst A. Catalyst E contained 0.42 weight-% Ti and 0.33 weight-% Pt.

Catalyst F (Control) was prepared substantially in accordance with Catalyst D, except that the material which had been treated with EADC and heated at 650° C. in He was subsequentially treated as follows: first heated in He (to 200° C.), heated in 80/20 He/HCl so as to raise the temperature from 200° C. to 550° C. within 35 minutes, and then heated in 80/20 He/HCl at 550° C. for 1 hour, followed by cooling in 80/20 He/HCl from 550° C. to 200° C. within 35 minutes and cooling in He from 200° C. to 180° C. Catalyst F contained 0.45 weight-% Ti and 0.34 weight-% Pt.

Catalyst G (Control) was prepared substantially in accordance with the procedure for Catalyst F, except that the treatment with the He/HCl was carried out at 400° C. (rather than 550° C.), and the HCl-treated material was subsequently heated in 80/20 He/$CCl_4$ at 200° C. for 1 hours. Catalyst F contained 0.42 weight-% Ti and 0.33 weight-% Pt.

Catalyst H (Control) was prepared substantially in accordance with the procedure for Catalyst F, except that the heating in He after EADC-treatment was carried out at 550° C. (in lieu of 650° C.). Catalyst H contained 0.42 weight-% Ti and 0.33 weight-% Pt.

Catalyst I (Invention) was prepared by mixing 15.00 grams (20 cc) of Criterion alumina with an aqueous solution of "TYZOR" (a registered trademark of DuPont) TE TITANATE (both described in the preparation of Catalyst C). The obtained mixture was dried/calcined, impregnated with an aqueous $H_2PtCl_4$ solution, dried and calcined (as described for Catalyst C). The Pt-impregnated material was treated with 7.00 grams of a 30 weight-% solution of EADC in cyclohexane for about 30 minutes under an argon gas atmosphere, followed by drying the EADC-treated material at room temperature in an argon stream for 18 hours, heating it in an He gas stream at 662° C. for 1 hour, and cooling it to 150° C. under He gas within a period of 1 hour. 16.06 grams of the EADC-treated material was then treated as follows: heating from room temperature to 200° C. to 550° C. with 80/20 He/HCl within 1 hour, heating at 550° C. with 80/20 He/HCl for 1 hour, cooling in 80/20 He/HCl from 550° C. to 200° C. at a rate of 5° C./minute, heating from 200° C. to 300° C. in 80/20 He/$CCl_4$ within 1 hour, cooling from 300° C. to 200° C. in He/$CCl_4$ within 1 hour, and cooling in He to 100° C. Catalyst I contained 0.42 weight-% Ti and 0.33 weight-% Pt.

Catalyst K (Invention) was prepared substantially in the same manner as Catalyst I, with the following exceptions: the weight of the alumina starting material was 16.0 grams, the HCl-treated material was heated in He while the temperature was raised from room temperature to 300° C., then heated in He at 300° C. for 10 minutes, thereafter heated in 80/20 He/$CCl_4$ at 300° C. for 1 hour, and cooled from 300° C. to 180° C. in He. Catalyst K contained 0.45 weight-% Ti and 0.34 weight-% Pt.

Catalyst L (Invention) was prepared substantially in the same manner as Catalyst I, with the following exceptions: the weight of the alumina starting material was 29.0 grams, the weight of the EADC solution was 14.0 grams, the HCl-treated material was heated in 80/20 He/$CCl_4$ from 200° C. to 300° C. at a rate of 5° C./minute, then heated in 80/20 He/$CCl_4$ at 300° C. for 1 hour, and thereafter cooled in 80/20 He/$CCl_4$ from 300° C. to 200° C. and in pure He from 200° C. to 180° C. Catalyst L contained 0.55 weight-% Ti and 0.33 weight-% Pt.

Catalyst M (Control) was prepared substantially in accordance with the procedure for Catalyst L, except that the weight of the $Al_2O_3$ starting material was 29.0 grams and the weight of the EADC solution was 14.0 grams. Catalyst M contained 0.69 weight-% Ti and 0.33 weight-% Pt.

EXAMPLE II

This example illustrates the use of the catalyst materials described in Example I in the isomerization of n-butane.

20 cc of each catalyst was placed in a stainless steel reactor tube having an inner diameter of 1 inch and a length of 28 inches. The steel reactor tube was heated to 138° C. A stream of hydrogen gas was passed through the catalyst bed at a rate of 1.34 cubic fee per hour. The reactor pressure was about 500 psig, Liquid n-butane was introduced at a rate of 78.2 cc/hour (liquid hourly space velocity:3.9 cc/cc catalyst/ hour), while the flow of the hydrogen gas stream was maintained at 1.34 $ft^3$/hour so as to provide a molar ratio of $H_2$ to n-butane of about 50:1. After the hydrogen/n-butane mixture had passed through the catalyst bed at the above conditions for about 10 minutes, carbon tetrachloride was injected into this feed mixture at a rate of 16 microliters per hour for a time period of up to about 24 hours. Thereafter, the $CCl_4$ feed rate was reduced to 6 microliters per hour, and the test was continued. The isomerization product was analyzed by means of a gas chromatograph. Pertinent catalyst preparation parameters and isomerization test results (obtained at comparable reaction times) are summarized in Table I.

TABLE I

| Catalyst | Wt-% Ti in Catalyst | Temperature (°C.) of Catalyst Preparation Step | | | n-Butane Isomerization | |
|---|---|---|---|---|---|---|
| | | EADC Treatment | HCl Treatment | $CCl_4$ Treatment | Reaction Time (hr.) | % of Isobutane in Product |
| A (Control) | 0 | 650 | 550 | 300 | 14 | 4.5 |
| B (Control) | 0 | 650 | 550 | 300 | 22 | 7.9 |
| C (Control) | 0.42 | None | None | None | 20 | 0.4 |
| D (Control) | 0.42 | 650 | None | None | 21 | 7.1 |
| E (Control) | 0.42 | 650 | None | 300 | 20 | 3.3 |
| F (Control) | 0.45 | 650 | 550 | None | 21 | 1.4 |
| G (Control) | 0.42 | 650 | 400 | 200 | 20 | 4.5 |
| H (Control) | 0.42 | 550 | 550 | 300 | 20 | 1.5 |
| I (Invention) | 0.42 | 650 | 550 | 300 | 20 | 16.3 |
| K (Invention) | 0.45 | 650 | 550 | 300 | 18 | 13.2 |
| L (Invention) | 0.55 | 650 | 550 | 300 | 22 | 10.5 |
| M (Control) | 0.69 | 650 | 550 | 300 | 20 | 1.3 |
| I-8[1] | N/A[2] | N/A[2] | N/A[2] | N/A[2] | 20 | 12.9 |
| I-8[1] | N/A[2] | N/A[2] | N/A[2] | N/A[2] | 19 | 11.1 |

[1] Commercial $Pt/Cl/Al_2O_3$ catalyst for butane isomerization containing about 0.3 weight-% Pt, marketed by UOP, De Plains, IL.
[2] No information available.

Test data in Table I show that a specific combination of preparation parameters (incorporation of about 0.4–0.6 weight-% Ti, EADC treatment at about 650° C., HCl treatment at about 550° C. and $CCl_4$ treatment at about 300° C.) resulted in invention catalysts G, H and I which exhibited high n-butane isomerization activity (comparable to that of a commercial catalyst, UOP's I-8).

Reasonable variations, modifications, and adaptations for various usages and conditions can be made within the scope of the disclosure and the appended claims without departing from the scope of this invention.

That which is claimed:

1. A method of preparing a solid composition consisting essentially of the sequence of steps of:
   (a) impregnating alumina with at least one dissolved titanium compound and at least one platinum compound;
   (b) calcining the impregnated alumina obtained in step (a) at a temperature of about 300°–650° C. for a time period of at least 10 minutes;
   (c) contacting the material obtained in step (b) with at least one organoaluminum chloride which is dissolved in an essentially water-free solvent;
   (d) calcining the treated material obtained in step (c) at a temperature of about 600°–700° C. for a time period of at least about 10 minutes;
   (e1) treating the material obtained in step (d) with a HCl-containing gas at a temperature of about 500°–600° C. for a time period of at least about 10 minutes; and
   (e2) treating the material obtained in step (e1) with a gas containing at least one chloroalkane at a temperature of about 250°–350° C. for a time period of at least about 10 minutes;
   wherein said solid composition prepared by said method comprises about 0.4–0.6 weight-% Ti.

2. A method in accordance with claim 1, wherein said solid composition comprises about 0.1–1 weight-% Pt and about 2–7 weight-% Cl.

3. A method in accordance with claim 2, wherein said at least one dissolved titanium compound employed in step (a) is at least one dissolved alkanolamine titanate.

4. A method in accordance with claim 3, wherein step (a) is carried out in three sub-steps: (a1) alumina is first impregnated with said at least one dissolved alkanolamine titanate, (a2) the titanate-impregnated alumina material obtained in step (a1) is calcined at a temperature of about 300°–600° C. for a time period of at least about 10 minutes, and (a3) the calcined material obtained in step (a2) is impregnated with at least one dissolved platinum compound.

5. A method in accordance with claim 4, wherein said at least one dissolved alkanolamine titanate is a dissolved triethanolamine titanate.

6. A method in accordance with claim 5, wherein said triethanolamine titanate is diisopropyl-bis(triethanolamine) titanate.

7. A method in accordance with claim 3, wherein step (b) is carried out at a temperature of about 450°–550° C. for a time period of about 0.5–20 hours.

8. A method in accordance with claim 3, wherein said at least one organoaluminum chloride used in step (c) is ethylaluminum dichloride.

9. A method in accordance with claim 8, wherein step (c) is carried out at a weight ratio of ethylaluminum dichloride to the calcined material obtained in step (b) of about 0.05:1 to about 1:1.

10. A method in accordance with claim 9, wherein step (c) is carded out at a temperature of about 10°–50° C. for a time period of about 0.5–5 hours.

11. A method in accordance with claim 3, wherein step (d) is carried out at a temperature of about 625°–675° C. for a time period of about 0.5–20 hours.

12. A method in accordance with claim 3, wherein said at least one chloroalkane employed in step (e2) is carbon tetrachloride.

13. A method in accordance with claim 12, wherein step (e1) is carried with a gas containing about 10–30 weight-% HCl and an inert gas as the remainder, at a temperature of about 525°–575° C. for a time period of about 0.2–20 hours.

14. A method in accordance with claim 12, wherein step (e2) is carried out with a gas containing about 10–30 weight-% $CCl_4$ and an inert gas as the remainder, at a temperature of about 275°–325° C. for a time period of about 0.2–20 hours.

15. A composition of matter prepared by the method of claim 1.

16. A composition of matter prepared by the method of claim 2.

17. A composition of matter prepared by the method of claim 3.

18. A composition of matter prepared by the method of claim 5.

19. A composition of matter prepared by the method of claim 8.

20. A composition of matter prepared by the method of claim 12.

21. A method in accordance with claim 1, wherein said at least one chloroalkane contains 1–4 carbon atoms and 1–6 chlorine atoms per molecule.

22. A method in accordance with claim 21, wherein said at least one chloroalkane is selected from the group consisting of chloromethane, dichloromethane, trichloromethane, carbon tetrachloride, chloroethane, 1,1-dichloroethane, 1,2-dichloroethane, trichloroethanes, tetrachloroethanes, hexachloroethane, -chloropropane, 2-chloropropane, 1,2-dichloropropane, 1,3-dichloropropane, 2,2-dichloropropane, trichloropropanes, tetrachloropropanes, chlorobutanes, 1-chloro-2-methyl-propane, dichlorobutanes, trichlorobutanes, tetrachlorobutanes, and mixtures thereof.

23. A composition of matter prepared by the method of claim 4.

24. A composition of matter prepared by the method of claim 6.

25. A composition of matter prepared by the method of claim 7.

26. A composition of matter prepared by the method of claim 9.

27. A composition of matter prepared by the method of claim 10.

28. A composition of matter prepared by the method of claim 11.

29. A composition of matter prepared by the method of claim 13.

30. A composition of matter prepared by the method of claim 14.

31. A composition of matter prepared by the method of claim 21.

* * * * *